United States Patent
Alexander

[11] Patent Number: 5,993,418
[45] Date of Patent: Nov. 30, 1999

[54] SAFETY SYRINGE

[75] Inventor: Gary E. Alexander, Baton Rouge, La.

[73] Assignee: Medisys Technologies, Inc., Baton Rouge, La.

[21] Appl. No.: 09/028,605

[22] Filed: Feb. 24, 1998

[51] Int. Cl.[6] .......................... A61M 5/00; A61M 5/178; A61M 5/32
[52] U.S. Cl. ....................... 604/110; 604/164; 604/195; 604/198; 604/272
[58] Field of Search .................... 604/110, 164, 604/192, 195, 196, 198, 218, 240, 263, 264, 272

[56] References Cited

U.S. PATENT DOCUMENTS

| | | |
|---|---|---|
| 3,094,122 | 6/1963 | Gauthier et al. ............... 128/221 |
| 3,368,558 | 2/1968 | Sarnoff et al. ............... 128/218 |
| 4,026,287 | 5/1977 | Haller ............... 128/215 |
| 4,197,846 | 4/1980 | Bucalo ............... 128/218 |
| 4,425,120 | 1/1984 | Sampson et al. ............... 604/198 |
| 4,464,171 | 8/1984 | Garwin ............... 604/53 |
| 4,581,021 | 4/1986 | Landau et al. ............... 604/212 |
| 4,636,202 | 1/1987 | Lowin et al. ............... 604/236 |
| 4,702,738 | 10/1987 | Spencer ............... 604/198 |
| 4,737,150 | 4/1988 | Baeumle et al. ............... 604/198 |
| 4,846,785 | 7/1989 | Cassou et al. ............... 600/34 |
| 4,846,799 | 7/1989 | Tanaka et al. ............... 604/158 |
| 4,850,996 | 7/1989 | Cree ............... 604/198 |
| 4,863,434 | 9/1989 | Bayless et al. ............... 604/198 |
| 4,863,435 | 9/1989 | Sturman et al. ............... 604/198 |
| 4,874,382 | 10/1989 | Lindemann et al. ............... 604/195 |
| 4,875,896 | 10/1989 | Kurtz ............... 604/187 |
| 4,883,471 | 11/1989 | Braginetz et al. ............... 604/195 |
| 4,883,472 | 11/1989 | Michel ............... 604/208 |
| 4,892,107 | 1/1990 | Haber ............... 128/763 |
| 4,894,055 | 1/1990 | Sudnak ............... 604/198 |
| 4,909,791 | 3/1990 | Norelli ............... 604/192 |
| 4,909,792 | 3/1990 | Norelli ............... 604/192 |
| 4,923,445 | 5/1990 | Ryan ............... 604/195 |
| 4,929,237 | 5/1990 | Medway ............... 604/198 |
| 4,935,014 | 6/1990 | Haber ............... 604/195 |
| 4,935,016 | 6/1990 | Deleo ............... 604/198 |
| 4,936,830 | 6/1990 | Verlier ............... 604/110 |
| 4,944,723 | 7/1990 | Haber et al. ............... 604/110 |
| 4,966,592 | 10/1990 | Burns et al. ............... 604/198 |
| 4,966,593 | 10/1990 | Lennox ............... 604/198 |
| 4,969,877 | 11/1990 | Kornberg ............... 604/195 |
| 4,973,316 | 11/1990 | Dysarz ............... 604/195 |
| 4,973,317 | 11/1990 | Bobrove ............... 604/198 |
| 4,976,701 | 12/1990 | Ejlersen et al. ............... 604/192 |
| 4,982,842 | 1/1991 | Hollister ............... 206/365 |
| 4,986,819 | 1/1991 | Sobel ............... 604/198 |
| 4,994,034 | 2/1991 | Botich et al. ............... 604/110 |
| 4,994,041 | 2/1991 | Dombrowski et al. ............... 604/164 |
| 5,015,240 | 5/1991 | Soproni et al. ............... 604/192 |
| 5,026,353 | 6/1991 | Bartman ............... 604/192 |
| 5,032,117 | 7/1991 | Motta ............... 604/88 |
| 5,049,133 | 9/1991 | Villen Pascual ............... 604/110 |
| 5,051,109 | 9/1991 | Simon ............... 604/263 |
| 5,067,942 | 11/1991 | Jaffe et al. ............... 604/110 |
| 5,092,851 | 3/1992 | Ragner ............... 604/192 |
| 5,092,852 | 3/1992 | Poling ............... 604/192 |
| 5,098,401 | 3/1992 | De Lange ............... 604/192 |
| 5,104,384 | 4/1992 | Parry ............... 604/192 |
| 5,122,123 | 6/1992 | Vaillancourt ............... 604/192 |
| 5,135,507 | 8/1992 | Haber et al. ............... 604/187 |
| 5,151,088 | 9/1992 | Allison et al. ............... 604/192 |
| 5,188,599 | 2/1993 | Botich et al. ............... 604/110 |
| 5,205,825 | 4/1993 | Allison ............... 604/110 |
| 5,256,152 | 10/1993 | Marks ............... 604/198 |
| 5,282,792 | 2/1994 | Imbert ............... 604/187 |
| 5,300,038 | 4/1994 | Haber et al. ............... 604/187 |
| 5,306,258 | 4/1994 | de la Fuente ............... 604/198 |
| 5,314,503 | 5/1994 | Bobrove et al. ............... 604/164 |
| 5,342,320 | 8/1994 | Cameron ............... 604/192 |
| 5,370,628 | 12/1994 | Allison ............... 604/192 |
| 5,383,851 | 1/1995 | McKinnon, Jr. et al. ............... 604/68 |
| 5,385,555 | 1/1995 | Hausser ............... 604/192 |
| 5,407,431 | 4/1995 | Botich et al. ............... 604/110 |
| 5,460,611 | 10/1995 | Alexander ............... 604/110 |
| 5,503,627 | 4/1996 | McKinnon et al. ............... 604/72 |
| 5,520,639 | 5/1996 | Peterson et al. ............... 604/68 |
| 5,540,660 | 7/1996 | Jenson ............... 604/110 |
| 5,665,072 | 9/1997 | Yoon ............... 604/164 |
| 5,720,727 | 2/1998 | Alexander ............... 604/110 |

FOREIGN PATENT DOCUMENTS

WO 89/08468  9/1989  WIPO .

OTHER PUBLICATIONS

U.S. application No. 08/656,848, Alexander, filed May 30, 1996.

U.S. application No. 08/886,393, Alexander, filed Nov. 14, 1996.

*Primary Examiner*—Corrine McDermott
*Assistant Examiner*—Michael J. Hayes
*Attorney, Agent, or Firm*—Roy, Kiesel & Tucker

[57] ABSTRACT

A safety syringe is disclosed. The safety syringe has a hollow barrel and a plunger. The plunger enters the barrel from one end and a retractable needle leaves the barrel from the other end. A blunt sheath is positioned over the needle. The needle has an exposed position in which the point of the needle extends beyond the sheath and a covered position in which the point of the needle is contained within the sheath. The plunger and the needle are configured to cause the needle to move from the exposed position to the covered position upon the depression of the plunger. In operation, the safety syringe may be filled like a conventional syringe by placing the needle in a vial of medication and retracting the plunger. Once the safety syringe is filled, the needle is inserted into the patient. In one embodiment, the sheath may be inserted into the patient with the needle. The medication is then injected into the patient by depressing the plunger. Depressing the plunger will, as stated, cause the needle to retract into the covered position.

24 Claims, 5 Drawing Sheets

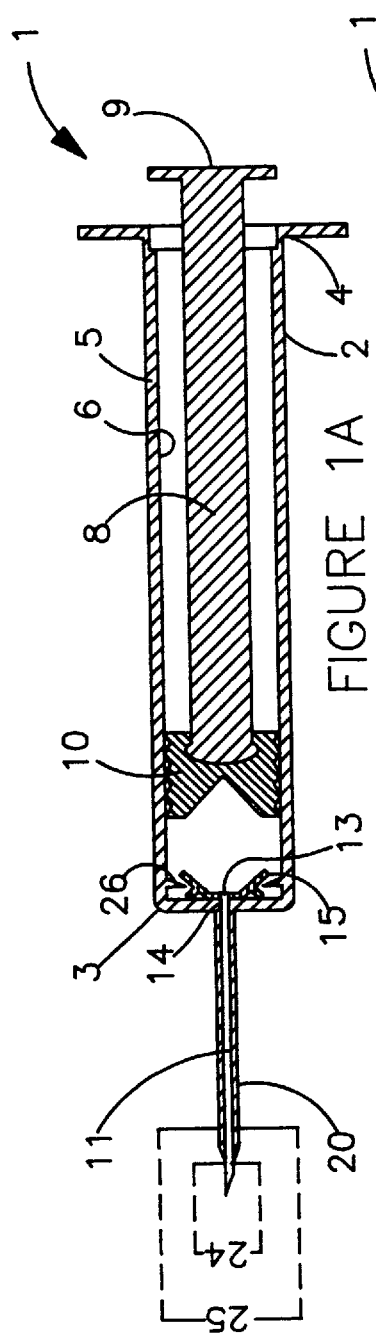
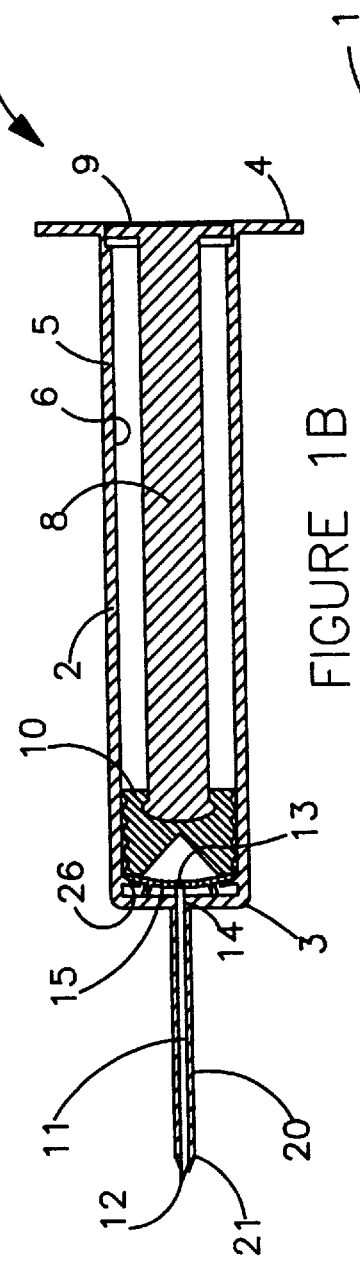
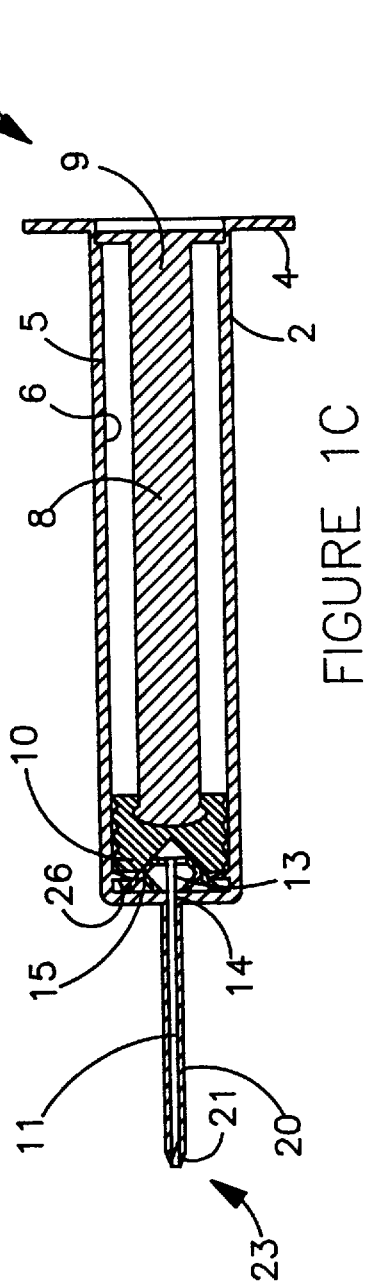

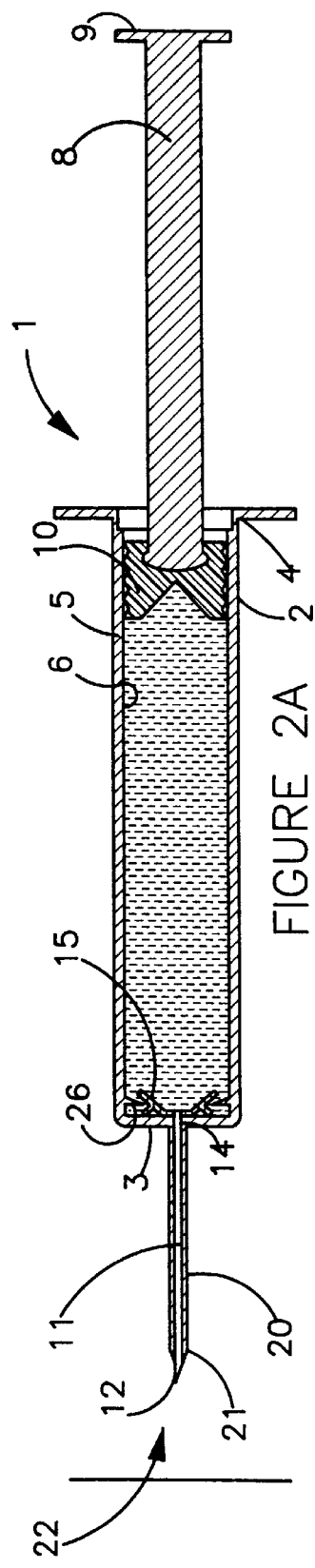
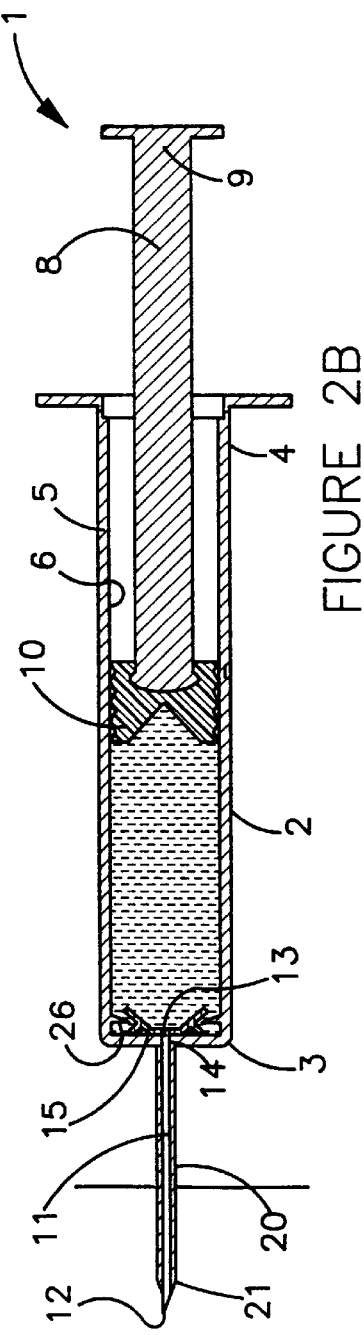

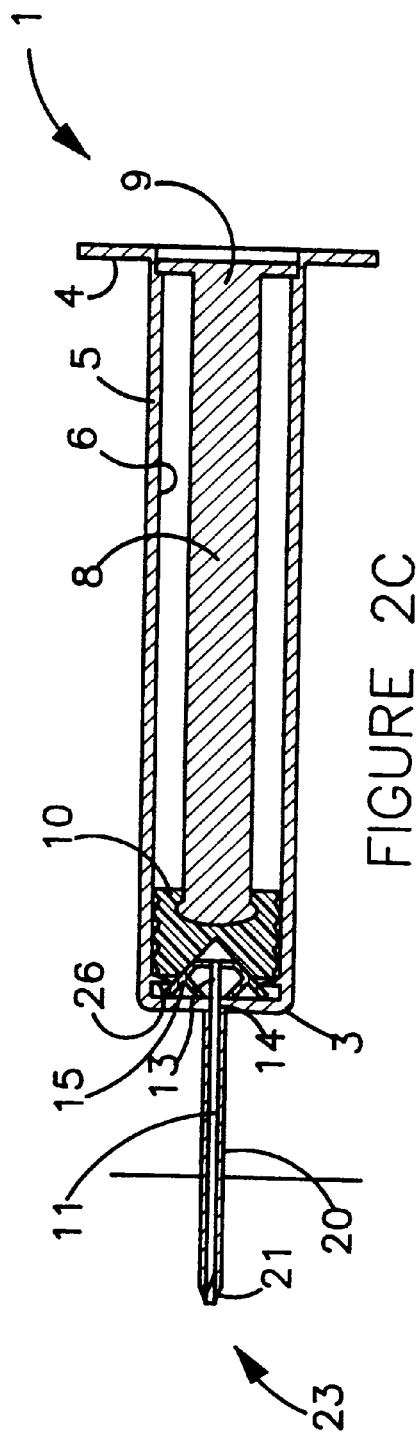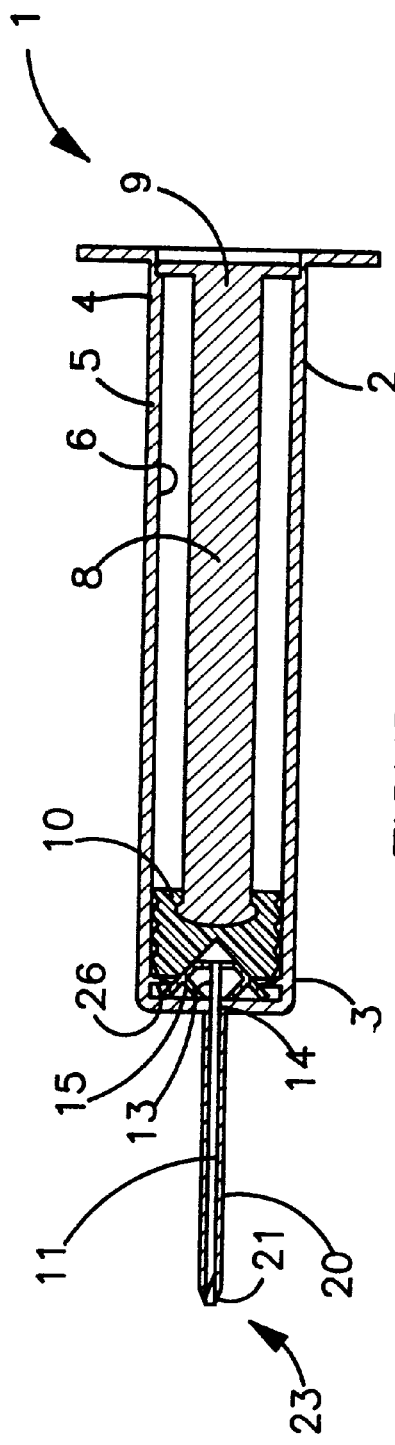

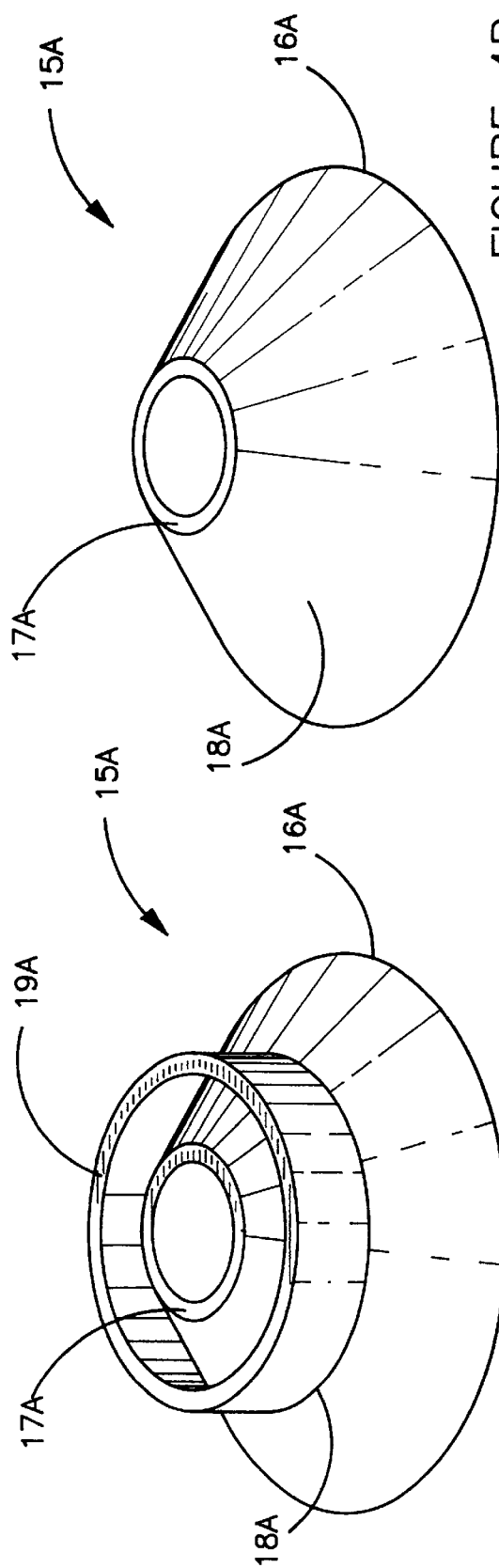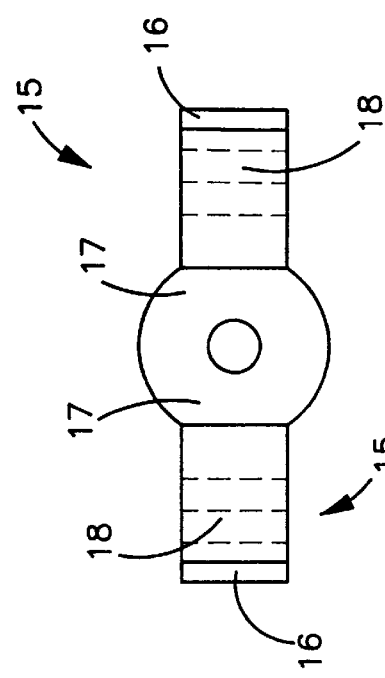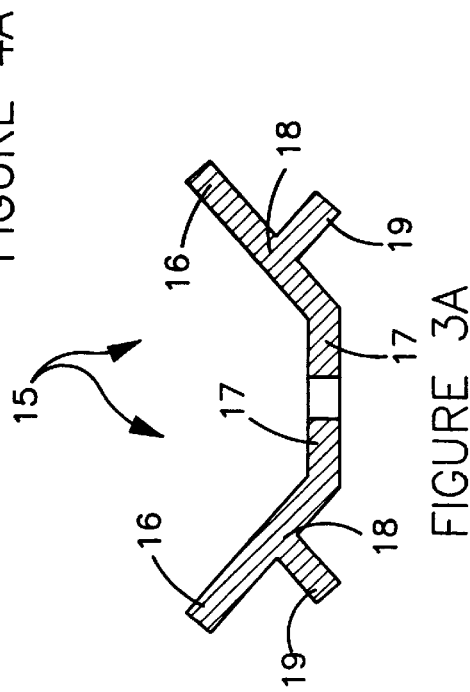

SAFETY SYRINGE

BACKGROUND OF THE INVENTION

1. Field of the Invention

The invention relates generally to hypodermic syringes and particularly to safety syringes designed to avoid accidental sticks.

2. Prior Art

The risk of contracting diseases such as HIV or hepatitis from accidental sticks with dirty needles is a potentially deadly hazard for medical professionals. Many syringe designs have been created that attempt to avoid or minimize this risk. Although most designs provide safety advantages over the conventional syringe, many come with substantial drawbacks. One of the most serious is the length of time between the completion of the injection and the covering of the needle. During this period, a window of opportunity exists for an accidental stick. Frequently, the minimization of this window comes at the price of creating a complicated syringe that is operated quite differently from a conventional syringe. The complicated designs often result in a syringe that is expensive to manufacture. The presence of these short comings in the prior art gives rise to the need for a safety syringe meeting the following objectives.

OBJECTS OF THE INVENTION

It is an object of the invention to provide a safety syringe that minimizes the window of opportunity for an accidental stick.

It is an object of the invention to provide a safety syringe that automatically covers the needle upon the administration of the injection.

It is a another object of the invention to provide a safety syringe that can cover the needle prior to its removal from the patient.

It is another object of the invention to provide a safety syringe that will cover the needle upon depression of the plunger.

It is another object of the invention to cover the needle by retracting it within a sheath upon depression of the plunger.

It is another object of the invention to provide a safety syringe that can be operated with one hand.

It is another object of the invention to provide a safety syringe that can be used like a conventional syringe.

It is yet another object of the invention to provide a safety syringe that can be used to draw up medications and to purge air from the syringe.

It is still another object of the invention to provide a safety syringe that is relatively easy and inexpensive to manufacture and that is simple in operation.

These and other objects and advantages of the invention shall become obvious from the figures and from the following descriptions of the preferred embodiments of the invention.

SUMMARY OF THE INVENTION

A safety syringe is disclosed. The safety syringe is comprised of an elongated hollow barrel having a needle end and a plunger end. (The term "end" is used repeatedly herein. It is intended to refer to a general region or portion of the object described rather than the absolute terminus of the object unless otherwise indicated). A plunger is insertable into the plunger end of the barrel. The end of the plunger is fitted to the inside of the barrel so that it creates a fluid tight seal between it and the interior wall of the barrel. A needle extends from the needle end of the barrel. The barrel end of the needle is contained within the barrel while the sharp end is external to the barrel so that the needle provides fluid passage from the interior of the barrel to its exterior. Thus, the contents of the syringe may be evacuated through the needle by depressing the plunger. By inserting the needle into the desired object and depressing the plunger, the contents of the needle may be injected into that object.

The needle is slidably disposed within the needle end of the barrel. The needle has two positions, an extended position and a retracted position. Initially the needle is positioned. in its extended position relative to the barrel. The needle is configured to retract relative to the barrel upon depression of the plunger. Preferably, this is accomplished by operation of a retraction lever extending from the barrel end of the needle.

The lever is preferably provided with a fulcrum point such that motion at one end of the lever will cause motion in the opposite direction at the opposite end of the lever. On either side of the fulcrum point are a retraction end and a control end of the lever. In a preferred embodiment, the retraction end is connected to the needle at a point spaced at least slightly above the needle end of the barrel. The fulcrum point is preferably braced against the needle end of the barrel by a fulcrum while the control end extends from the fulcrum point to within the barrel. The plunger will encounter the control end of the lever as the plunger is depressed. Continued depression of the plunger will depress the control end of the lever. This will cause the lever to pivot on the fulcrum point which in turn will elevate the retraction end of the lever and drive the needle toward the plunger end of the barrel.

A hollow sheath having a tip end and a barrel end extends from the needle end of the barrel and is disposed over the needle. The sheath is configured so that the sharp end of the needle extends from the sheath when the needle is in its exposed position. The sheath is further configured so that the sharp end of the needle is contained within the sheath when the needle is in its covered position. Thus, by depressing the plunger the needle may be retracted to a position where the needle is covered by the sheath.

In a preferred embodiment, the sheath is relatively thin. It should be thin enough that it may be inserted with the needle into the patient when an injection is given, in much the same way as a catheter is inserted. In a preferred embodiment, the sheath should have an external diameter at the tip end of between about 110% and 150% of the external diameter of the needle. When this embodiment is used, the needle can be covered prior to its removal from the patient. Thus, after the injection, there is never a contaminated sharp needle exposed, and the possibility for accidental sticks is greatly reduced.

BRIEF DESCRIPTION OF THE DRAWINGS

FIG. 1A is cross sectional view of a preferred embodiment of the invention just prior to the engagement of the control end of the lever by the washer end of the plunger.

FIG. 1B is a cross sectional view of a preferred embodiment of the invention during the movement of the needle from its exposed position to its covered position.

FIG. 1C is a cross sectional view of a preferred embodiment of the invention after the plunger has been fully depressed.

FIG. 2A is a cross sectional view of a preferred embodiment of the invention prior to the administration of an injection to a patient.

FIG. 2B is a cross sectional view of a preferred embodiment of the invention during the administration of an injection to a patient.

FIG. 2C is a cross sectional view of a preferred embodiment of the invention at the conclusion of the administration of an injection to a patient.

FIG. 2D is a cross sectional view of a preferred embodiment of the invention upon withdrawal of the syringe from a patient after the administration of an injection.

FIG. 3A is a side view of a preferred embodiment of a lever.

FIG. 3B is a top view of a preferred embodiment of a lever.

FIG. 4A is a perspective view of a conical version of a lever.

FIG. 4B is a perspective view of another conical version of a lever.

DETAILED DESCRIPTION OF THE PREFERRED EMBODIMENT OF THE INVENTION

Figure 5:
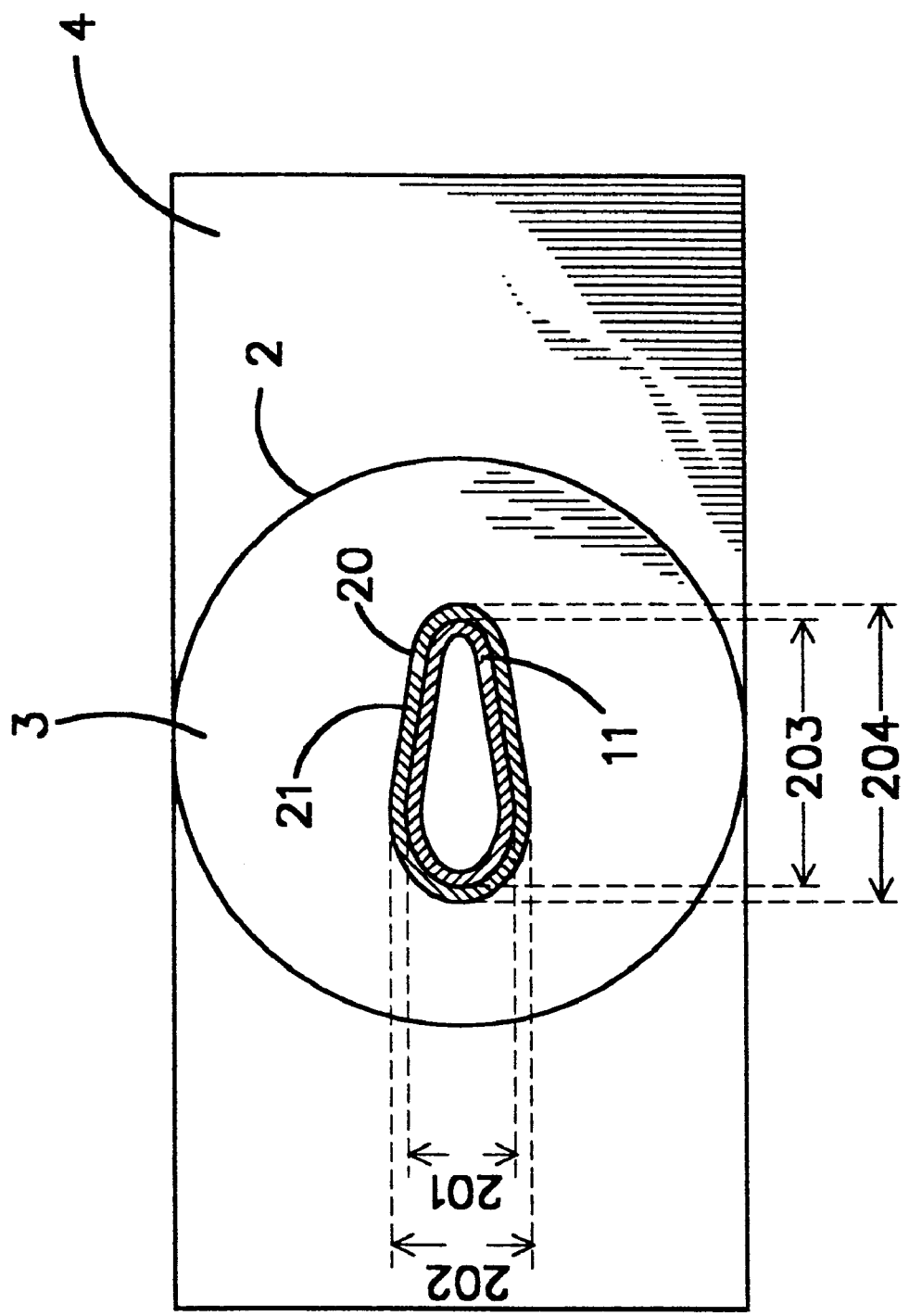
FIG. 5 is a bottom view of one preferred embodiment of the invention.

A safety syringe 1 is disclosed. Safety syringe 1 comprises a substantially hollow barrel 2 having a needle end 3, a plunger end 4, a wall 5, and an interior surface 6 of wall 5. Needle end 3, plunger end 4 and interior surface 6 define a fluid receiving cavity within barrel 2. In a preferred embodiment, calibrated measurement lines are marked on wall 5. In a preferred embodiment, barrel 2 is made of transparent or translucent plastic.

A plunger 8 fits within barrel 2. Plunger 8 has a thumb end 9 and a washer end 10. Washer end 10 is sized to engage interior surface 6 of barrel 2 so that a substantially fluid tight seal is created between washer end 10 and interior surface 6. In a preferred embodiment, washer end 10 is made of or covered with rubber while plunger 8 is made of a harder plastic. In another preferred embodiment plunger 8 and washer end 10 are a single composite unit. Upon insertion of plunger 8 into barrel 2, the volume of the fluid receiving cavity may be varied by operation of plunger 8.

A hollow needle 11 having a sharp end 12 and a barrel end 13 is slidably disposed in needle end 3 of barrel 2 through a needle aperture 14. Barrel end 13 of needle 11 is positioned within barrel 2 and pointed end 12 is positioned external of barrel 2. Thus, needle 11 provides fluid passage into and out of barrel 13.

The connection between needle 11 and needle end 3 of barrel 2 should satisfy several criteria. First, it should be fluid tight under normal injection pressures. Second, it should hold needle 11 in place relative to needle end 3 of barrel 2 while needle 11 is puncturing skin and tissue during the administration of an injection. Third, it should allow needle 11 to be retracted upon the application of force normally associated with the depression of plunger 8 during the administration of an injection using the mechanical configurations described more thoroughly below. The satisfaction of these criteria is a function of the friction coefficient between needle 11 and the needle aperture 14. Assuming that a conventional needle is used, the friction coefficient will depend upon the diameter and length of needle aperture 14 and the material used to make needle end 3 of barrel 2. The inventor contemplates making needle end 3 of barrel 2 out of a rubber or plastic capable of forming the fluid tight seal with needle 11 required of needle end 3. In one preferred embodiment, the entire barrel 2 may be made out of the same material as needle end 3.

Safety syringe 1 is provided with a means for retracting needle 11 upon the depression of plunger 8. This preferably entails at least one and preferably two or more levers 15. Lever 15 has a control end 16 and a retraction end 17. Retraction end 17 is attached to barrel end 13 of needle 11, preferably with an adhesive or other conventional means. Lever 15 should preferably be attached to needle 11 prior to the insertion of needle 11 into needle end 3 of barrel 2. The connection between retraction end 17 and needle 11 is preferably hinged or otherwise rendered pivotal. Lever 15 should preferably be made from plastic.

Between retraction end 17 and control end 16 of lever 15 is a fulcrum point 18 resting, over a fulcrum 19. Lever 15 should preferably be initially positioned so that control end 16 is further from needle end 3 of barrel 2 than retraction end 17 and fulcrum point 18. Lever 15 should also preferably be initially positioned so that retraction end 17 is positioned closer to needle end 3 of barrel 2 than fulcrum point 18. Fulcrum 19 should preferably rest against or extend from needle end 3 of barrel 2. When positioned as described, a downward force delivered to control end 16 of lever 15 would cause it to pivot on fulcrum 19 at fulcrum point 18 such that retraction end 17 of lever 15 would be driven rearward. When retraction end 17 of lever 15 is attached to barrel end 13 of needle 11, the rearward movement of retraction end 17 will cause needle 11 to slide in needle end 3 of barrel 2 toward plunger end 4 of barrel 2.

Force can be exerted upon control end 16 of lever 15 by washer end 10 of plunger 8 As plunger 8 is depressed, plunger 8 will engage control end 16 of lever 15. Continued depression of plunger 8 will cause control end 16 of lever 15 to move toward needle end 3 of barrel 2 which in turn will cause lever 15 to pivot on fulcrum 19 at fulcrum point 18. Retraction end 17 of lever 15 will move toward plunger end 4 of barrel 2 taking needle 11 with it as described above. Washer end 10 of plunger 8 preferably contains a central recession to receive barrel end 13 of needle 11 and retraction end 17 of lever 15. In this configuration, the perimeter of washer end 10 can engage control end 16 of lever 15 without washer end 10 impeding the retraction of needle 11.

Another means for retracting needle 11 upon the depression of plunger 8 comprises a conical version 15A of lever 15. Conical lever 15A has a control end 16A and a retraction end 17A. In operation, retraction end 17A will attach to needle 11 at or near needle end 3 of barrel 2. Conical lever 15A should have a fulcrum point 18A located near retraction end 17A that is preferably braced against needle end 3 of barrel 2 by a fulcrum 19A. Control end 16A of conical lever 15A will extend upward toward plunger 8 so that washer end 10 of plunger 8 will first encounter control end 16A of conical lever 15A during the depression of plunger. Conical lever 15A should be made of a flexible resilient material that will deform upon the application of pressure to control end 16A by plunger 8. Control end 16A will bend toward needle end 3 of barrel 2 as plunger 8 is depressed. At some point during the depression of plunger 8, the deformation of resilient conical lever 15A will cause retraction end 17A to snap upward to restore the conical shape of conical lever 15A. This motion will. invert the position of conical lever 15A relative to needle end 3 of barrel 2 such that control end 16A will be adjacent needle end 3 of barrel 2 while retraction end 17A will be separated from needle end 3 of barrel 2 by the height of conical lever 15A. Of course, moving retraction end 3 away from needle end 3 of barrel 2 will also cause needle 11 to move the same distance in the same direction.

A protective sheath 20 extends from needle end 3 of barrel 2. Needle 11 is disposed within sheath 20. Sheath 20 has a tip end 21 opposite barrel 2. Prior to the retraction of needle 11, at least a portion of sharp end 12 of needle 11 extends from tip end 21. This is the exposed position 22 of needle 11. Upon retraction of needle 11, sharp end 12 of needle 11 will be withdrawn into sheath 20. This is the covered position 23 of needle 11. Thus, needle 11 can be moved from exposed position 22 to covered position 23 simply by depressing plunger 8 as would ordinarily be done during the administration of an injection.

Needle 11 may be locked in covered position 23 by providing a detent arm 26 between plunger 8 and barrel 2 so that plunger 8 will be locked into place when it has been fully depressed. Alternatively or additionally, a detent mechanism might be positioned between needle 11 and needle end 3 of barrel 2 so that needle 11 might not re-extend into exposed position 22 after it has been retracted. Another means for preventing needle 11 from re-entering exposed position 22 would include making thumb end 9 of plunger 8 substantially headless or otherwise sizing thumb end 9 to allow plunger 8 to be inserted into the fluid receiving cavity inside barrel 2. This will help prevent the accidental retraction of plunger 8. All of the aforementioned means may help prevent accidental or intentional reuse of safety syringe 1.

In a preferred embodiment, sheath 20 is sized to be hypodermically insertable with needle 11. Needle 11 will have an external diameter 24. Likewise, sheath 20 will have an external diameter 25. While preferred embodiments of both needle 11 and sheath 20 are generally cylindrical, it is recognized that both may have other shapes such that their cross section is not a circle. When needle 11 and sheath 21 are not circular, needle 11 will have a shortest cross-sectional dimension 201 and a longest cross sectional dimension 203. Similarly, sheath 21 will have a shortest cross-sectional dimension 202 and a longest cross-sectional dimension 204. In such cases, diameter is intended herein to refer to the longest cross sectional dimension of the respective article unless otherwise indicated. External diameter 25 of sheath 20 at tip end 21 should be close enough to external diameter 24 of needle 11 to allow tip end 21 of sheath 20 to be inserted with needle 11 when safety syringe 1 is used to administer an injection. As needle 11 is inserted into tissue, it will create a puncture wound or tear in that tissue that is somewhat larger in diameter than external diameter 24 of needle 11. Sheath 20, and particularly tip end 21 should be sized to permit at least tip end 21 of sheath 20 to be inserted simultaneously with needle 11 into the puncture wound created by needle 11 during hypodermic injection.

In designing sheath 20, there are two competing goals, strength or puncture resistance and patient comfort. The thinner sheath 20 is, the more comfortable it will be for the patient when sheath 20 is inserted with needle 11 during injection, assuming the hypodermically insertable version of sheath 20 is in use. However, as sheath 20 is made thinner, it becomes less resistant to punctures and thus less able to perform its task of preventing accidental sticks. Therefore, a balance must be struck between these two competing goals when sheath 20 is designed. Of course, where this balance will fall will depend upon the characteristics of the materials used to make sheath 20. Currently, the inventors contemplate using plastic, Teflon®, or a metal such as braided stainless steel. However, other acceptable rigid or semi-rigid substances may be available now or developed in the future which may affect the thickness of sheath 20. Furthermore, it is anticipated that a non-rigid substance such as soft rubber which relies on needle 11 for its rigidity during insertion would perform adequately as a substance from which sheath 20 might be constructed. Sheath 20 may also be made from the same material as barrel 2 such that sheath 20 and barrel 2 could be constructed in a single composite piece.

When sheath 20 is to be hypodermically insertable, the thickness of sheath 20 will also vary with the size of needle 11. Needles come in twenty five standard gauges, where gauge is a measure of external diameter 24. Standard needles range from 30 gauge which has an external diameter of 12/1000 of an inch to 6 gauge which has an external diameter of 200/1000 of an inch. The incremental change in diameter between gauges is not uniform. For example, 29 gauge has a diameter of 13/1000 of an inch, only 1/1000 more than 30 gauge. At the other end of the spectrum, 7 gauge has an outer diameter of 180/1000 of an inch, 20/1000 less than 6 gauge.

Although safety syringe 1 may be used with any size needle 11, needles in the middle of the standard needle range—24 to 18 gauge—are expected to be used most often. A 24 gauge needle has an external diameter of 22/1000 while 18 gauge is 50/1000. When needle 11 falls into this middle range, it is anticipated that sheath 20, or at least tip end 21, should have an external diameter 25 of not more than about 150% of external diameter 24 of needle 11. In this size range, it is anticipated that the external diameter 25 of sheath 20, or at least tip end 21, should preferably be between about 118% and about 125% of external diameter 24 of needle 11. With larger needles 11, such as 6 or 7 gauge, it is expected that sheath 20 or tip end 21 should have an external diameter 25 of not more than about 133% and preferably about 110% of external diameter 24 of needle 11. It should be appreciated that the construction and composition of sheath 20 may allow it to be made thinner than the ranges given above in furtherance of the goal of patient comfort. Similarly, different construction and composition may force sheath 20 to be thicker in order to satisfy the goal of puncture resistance. Additional information regarding the construction of sheath 20 may be found in U.S. Pat. No. 5,460,611, PCT Application US95/11426, and allowed U.S. patent applications Ser. No. 08/727,756, now U.S. Pat. No. 5,720,727, and Ser. No. 08/746,580, now U.S. Pat. No. 5,846,228, all of which are hereby incorporated by reference in their entirety to the extent they are not contrary to the teachings herein.

In operation, safety syringe 1 will either come prefilled or it will come empty. A cap may be provided to protect sharp end 12 while needle 11 is in exposed position 22 prior to usage. The cap may also be used to help prevent leakage when prefilled versions of safety syringe 1 are used. If safety syringe 1 is empty, it will be filled in the same manner as a normal syringe, that is by inserting needle 11 into a vial of liquid medication and then withdrawing plunger 8 until the requisite amount of liquid is obtained. Once safety syringe 1 is full, any air trapped in the syringe should be expelled. This is done by pointing needle 11 up and depressing plunger 8 until a small amount of liquid is expelled from needle 11. At this point, safety syringe 1 is ready to be used.

The person administering the injection will sterilize the skin in the region that is to receive the injection. Needle 11 will then be inserted into the muscle or other tissue. Preferably, needle 11 will be inserted far enough so that tip end 21 of sheath 20 is also inserted into the tissue when the hypodermically insertable version of sheath 20 is used. To avoid unnecessarily deep injections, the distance between exposed position 22 and covered position 23 should be minimized although it should be noted that when a deep injection is needed, it may be desirable to configure sheath 20 so that substantially more than tip end 21 is insertable with needle 11. In a preferred embodiment, this distance between exposed position 22 and covered position 23 is about ⅛ of an inch. Once needle 11 is injected to the desired depth, plunger 8 will be depressed until washer end 10 engages control end 16 of lever 15. Continuing to depress plunger 8 will cause lever 15 to pivot on fulcrum 19 pushing retraction end 17 away from needle end 3 of barrel 2. Retraction end 17 will pull needle 11 in the same direction, thereby causing needle 11 to move from exposed position 22 to covered position 23. If the hypodermically insertable version of sheath 20 is used, needle 11 may be moved into covered position 23 prior to its removal from the patient. Additionally, if a detent mechanism, or other means for preventing needle 11 from re-entering exposed position 22 is used, needle 11 may be locked into place prior to its withdrawal from the patient.

It is anticipated that these and other uses and embodiments will be apparent to those skilled in the art in view of the foregoing description and drawings and are intended to be covered by the scope of the following claims.

I claim:

1. A safety syringe comprising:
    a substantially hollow barrel having a needle end, a plunger end, and a wall extending between said plunger end and said needle end, said wall having an interior surface, wherein said needle end, said plunger end and said interior surface of said wall define a fluid receiving cavity within said barrel;
    a plunger extending from said fluid receiving cavity of said barrel, said plunger having a thumb end and a washer end, said washer end configured to create a substantially fluid tight seal between said washer end and said interior wall of said barrel, whereby operation of said plunger will vary the volume of said fluid receiving cavity;
    a sheath extending from said needle end of said barrel, said sheath having a tip end, said tip end having an external diameter;
    a retractable needle extending from said needle end of said barrel into said sheath, said needle having a sharp end, a barrel end, and an external diameter; said needle having an exposed position wherein said sharp end of said needle extends beyond said tip end of said sheath, said needle further having a covered position wherein said sharp end of said needle is contained within said sheath; and
    a lever having a control end, a retraction end operatively attached to said barrel end of said needle, and a fulcrum point between said control end and said retraction end of said lever, wherein said control end of said lever is configured to operatively engage said plunger when said plunger is depressed, whereby said needle may be transferred from said exposed position to said covered position by the depression of said plunger.

2. A safety syringe according to claim 1 wherein said washer end of said plunger is configured to engage said control end of said lever upon the depression of said plunger whereby said lever can be pivoted about its fulcrum point to drive said retraction end of said lever and said needle toward said plunger end of said barrel.

3. A safety syringe according to claim 2 wherein said washer end contains a recession sized to receive said barrel end of said needle and said retraction end of lever.

4. A safety syringe according to claim 1 wherein said tip end of said sheath is sized to be hypodermically insertable with said needle.

5. A safety syringe according to claim 4 wherein said washer end of said plunger is configured to engage said control end of lever upon the depression of said plunger whereby said lever can be pivoted about its fulcrum point to drive said retraction end of said lever and said needle toward said plunger end of said barrel.

6. A safety syringe according to claim 5 wherein said washer end contains a recession sized to receive said barrel end of said needle and said retraction end of lever.

7. A safety syringe according to claim 4 wherein said tip end of said sheath has an external diameter of not more than about 150% of said external diameter of said needle.

8. A safety syringe according to claim 4 wherein said tip end of said sheath has an external diameter of not more than about 133% of said external diameter of said needle.

9. A safety syringe according to claim 4 wherein said tip end of said sheath has an external diameter that is between about 118% and about 125% of said external diameter of said needle.

10. A safety syringe according to claim 4 wherein said tip end of said sheath has an external diameter of about 110% of said external diameter of said needle.

11. A safety syringe according to claim 4 wherein said tip end has a shortest cross-sectional dimension, wherein said needle is capable of creating a puncture wound having a longest cross-sectional dimension during hypodermic injection, and wherein the shortest cross-sectional dimension of said tip end is less than the longest cross-sectional dimension of a puncture wound createable by said needle during hypodermic injection.

12. A safety syringe according to claim 4 wherein said tip end has a longest cross-sectional dimension, wherein said needle is capable of creating a puncture wound having a longest cross-sectional dimension during hypodermic injection, and wherein the longest cross-sectional dimension of said tip end is less than the longest cross-sectional dimension of a puncture wound createable by said needle during hypodermic injection.

13. A safety syringe comprising:
    a substantially hollow barrel having a needle end, a plunger end, and a wall extending between said plunger end and said needle end, said wall having an interior surface, wherein said needle end, said plunger end and said interior surface of said wall define a fluid receiving cavity within said barrel;
    a plunger extending from said fluid receiving cavity of said barrel, said plunger having a thumb end and a washer end, said washer end configured to create a substantially fluid tight seal between said washer end and said interior wall of said barrel, whereby operation of said plunger will vary the volume of said fluid receiving cavity;
    a sheath extending from said needle end of said barrel, said sheath having a tip end, said tip end having an external diameter;
    a retractable needle extending from said needle end of said barrel into said sheath, said needle having a sharp end, a barrel end, and an external diameter; said needle having an exposed position wherein said sharp end of said needle extends beyond said tip end of said sheath, said needle further having a covered position wherein said sharp end of said needle is contained within said sheath; and
    a means for transferring said needle from said exposed position to said covered position upon the depression of said plunger comprising a lever having a control end and a retraction end attached to said barrel end of said needle, said means further comprising a fulcrum point between said control end and said retraction end.

14. A safety syringe according to claim 13 wherein said washer end of said plunger is configured to engage said control end of said lever upon the depression of said plunger whereby said lever can be pivoted about its fulcrum point to drive said retraction end of said lever and said needle toward said plunger end of said barrel.

15. A safety syringe according to claim 14 wherein said washer end contains a recession sized to receive said barrel end of said needle and said retraction end of lever.

16. A safety syringe according to claim 13 wherein said tip end of said sheath is sized to be hypodermically insertable with said needle.

17. A safety syringe according to claim 16 wherein said washer end of said plunger is configured to engage said control end of said lever upon the depression of said plunger whereby said lever can be pivoted about its fulcrum point to drive said retraction end of said lever and said needle toward said plunger end of said barrel.

18. A safety syringe according to claim 17 wherein said washer end contains a recession sized to receive said barrel end of said needle and said retraction end of lever.

19. A safety syringe according to claim 16 wherein said tip end of said sheath has an external diameter of not more than about 150% of said external diameter of said needle.

20. A safety syringe according to claim 16 wherein said tip end of said sheath has an external diameter of not more than about 133% of said external diameter of said needle.

21. A safety syringe according to claim 16 wherein said tip end of said sheath has an external diameter that is between about 118% and about 125% of said external diameter of said needle.

22. A safety syringe according to claim 16 wherein said tip end of said sheath has an external diameter of about 110% of said external diameter of said needle.

23. A safety syringe according to claim 16 wherein said tip end has a shortest cross-sectional dimension, wherein said needle is capable of creating a puncture wound having a longest cross-sectional dimension during hypodermic injection, and wherein the shortest cross-sectional dimension of said tip end is less than the longest cross-sectional dimension of a puncture wound createable by said needle during hypodermic injection.

24. A safety syringe according to claim 16 wherein said tip end has a longest cross-sectional dimension, wherein said needle is capable of creating a puncture wound having a longest cross-sectional dimension during hypodermic injection, and wherein the longest cross-sectional dimension of said tip end is less than the longest cross-sectional dimension of a puncture wound createable by said needle during hypodermic injection.

* * * * *